US012364698B2

(12) United States Patent
Gole et al.

(10) Patent No.: US 12,364,698 B2
(45) Date of Patent: Jul. 22, 2025

(54) COMPOSITIONS CONTAINING IBRUTINIB

(71) Applicant: Janssen Pharmaceutica NV, Beerse (BE)

(72) Inventors: Dilip J. Gole, Plainsboro, NJ (US); Maristella Bernini, Beerse (BE); Sabine Inghelbrecht, Stekene (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 18/304,685

(22) Filed: Apr. 21, 2023

(65) Prior Publication Data

US 2023/0263804 A1 Aug. 24, 2023

Related U.S. Application Data

(60) Continuation of application No. 17/706,783, filed on Mar. 29, 2022, now abandoned, which is a continuation of application No. 16/708,929, filed on Dec. 10, 2019, now abandoned, which is a continuation of application No. 15/602,989, filed on May 23, 2017, now abandoned, which is a division of application No. 15/092,195, filed on Apr. 6, 2016, now abandoned.

(60) Provisional application No. 62/143,659, filed on Apr. 6, 2015.

(51) Int. Cl.

| A61K 31/519 | (2006.01) |
|---|---|
| A23L 33/10 | (2016.01) |
| A23L 33/16 | (2016.01) |
| A61J 3/07 | (2006.01) |
| A61K 9/00 | (2006.01) |
| A61K 9/10 | (2006.01) |
| A61K 9/48 | (2006.01) |
| A61K 47/02 | (2006.01) |
| A61K 47/12 | (2006.01) |
| A61K 47/38 | (2006.01) |
| B01J 2/10 | (2006.01) |
| B01J 2/22 | (2006.01) |

(52) U.S. Cl.
CPC ............ *A61K 31/519* (2013.01); *A23L 33/10* (2016.08); *A23L 33/16* (2016.08); *A61J 3/07* (2013.01); *A61K 9/0053* (2013.01); *A61K 9/10* (2013.01); *A61K 9/4858* (2013.01); *A61K 9/4866* (2013.01); *A61K 47/02* (2013.01); *A61K 47/12* (2013.01); *A61K 47/38* (2013.01); *B01J 2/10* (2013.01); *B01J 2/22* (2013.01); *A23V 2002/00* (2013.01); *A61K 9/4833* (2013.01)

(58) Field of Classification Search
None
See application file for complete search history.

(56) References Cited

U.S. PATENT DOCUMENTS

| 4,910,022 A | 3/1990 | Bavitz et al. |
|---|---|---|
| 5,994,348 A | 11/1999 | Ku et al. |
| 7,514,444 B2 | 4/2009 | Honigberg et al. |
| 8,003,309 B2 | 8/2011 | Ito et al. |
| 8,154,090 B2 | 4/2012 | Schuler et al. |
| 8,476,284 B2 | 7/2013 | Honigberg et al. |
| 8,497,277 B2 | 7/2013 | Honigberg et al. |
| 8,697,711 B2 | 4/2014 | Honigberg et al. |
| 8,703,780 B2 | 4/2014 | Honigberg et al. |
| 8,735,403 B2 | 5/2014 | Honigberg et al. |
| 8,754,090 B2 | 6/2014 | Buggy et al. |
| 8,754,091 B2 | 6/2014 | Honigberg et al. |

(Continued)

FOREIGN PATENT DOCUMENTS

| CN | 104039325 A | 9/2014 |
|---|---|---|
| CN | 104407067 A | 3/2015 |

(Continued)

OTHER PUBLICATIONS

Aalipour, A., et al. "Bruton's tyrosine kinase inhibitors and their clinical potential." Ther Adv Hemat. 2014 5(4) 121-133. (Year: 2014).

(Continued)

*Primary Examiner* — Nannette Holloman
(74) *Attorney, Agent, or Firm* — BakerHostetler

(57) ABSTRACT

Discussed herein are pharmaceutical compositions containing Ibrutinib and processes for preparing them. The compositions may be utilized in the treatment of a variety of conditions including, without limitation, B-cell proliferative disorders such as non-Hodgkin lymphoma (diffuse large B cell lymphoma, follicular lymphoma, mantle cell lymphoma or burkitt lymphoma), Waldenstrom macroglobulinemia, plasma cell myeloma, chronic lymphocytic leukemia, lymphoma, or leukemia. These compositions are designed for oral ingestion. The compositions are contained within a capsule such as a standard or sprinkle or in a liquid formulation such as a suspension. In one embodiment, the pharmaceutical composition contains Ibrutinib, a salt, prodrug, or metabolite thereof, microcrystalline cellulose, croscarmellose sodium, sodium lauryl sulfate, and magnesium stearate. In another embodiment, the pharmaceutical composition contains Ibrutinib, a salt, prodrug, or metabolite thereof, microcrystalline cellulose, carboxymethylcellulose sodium, hydroxypropylmethylcellulose, citric acid monohydrate, disodium hydrogen phosphate, sucralose, sodium methyl parahydroxybenzoate, sodium ethyl parahydroxybenzoate, concentrated hydrochloric acid, sodium hydroxide, and water.

27 Claims, 3 Drawing Sheets

(56) References Cited

U.S. PATENT DOCUMENTS

| | | | |
|---|---|---|---|
| 8,957,079 | B2 | 2/2015 | Honigberg et al. |
| 9,079,908 | B2 | 7/2015 | Honigberg et al. |
| 9,139,591 | B2 | 9/2015 | Honigberg et al. |
| 2011/0091539 | A1 | 4/2011 | Nagi et al. |
| 2014/0303191 | A1* | 10/2014 | Buggy .............. A61K 31/475 435/7.1 |
| 2015/0044217 | A1 | 2/2015 | Chen et al. |
| 2015/0140085 | A1 | 5/2015 | Goldstein |
| 2016/0022942 | A1 | 1/2016 | Millar et al. |
| 2016/0039838 | A1 | 2/2016 | Zhang et al. |
| 2019/0117579 | A1 | 4/2019 | Chong et al. |
| 2019/0282578 | A1 | 9/2019 | Atluri et al. |
| 2020/0171036 | A1 | 6/2020 | Gupta et al. |
| 2021/0032258 | A1 | 2/2021 | Purro et al. |

FOREIGN PATENT DOCUMENTS

| | | |
|---|---|---|
| CN | 104523695 A | 4/2015 |
| JP | 2014-205684 A | 10/2014 |
| JP | 2014-530877 A | 11/2014 |
| WO | 2013/184572 A1 | 12/2013 |
| WO | 2014/004707 A1 | 1/2014 |
| WO | 2014/177038 A1 | 11/2014 |
| WO | 2015/071432 A1 | 5/2015 |
| WO | 2015/140709 A1 | 9/2015 |
| WO | 2016/019341 A1 | 2/2016 |
| WO | 2016/022942 A1 | 2/2016 |
| WO | 2016/141068 A1 | 9/2016 |
| WO | 2016/164404 A1 | 10/2016 |
| WO | 2017/205843 A1 | 11/2017 |

OTHER PUBLICATIONS

Encyclopedia.com, citing The Columbia Encyclopedia 6th ed, 2009, available from: <https://www.encyclopedia.com/science-and-technology/biochemistry/biochemistry/metabolite >. Accessed Sep. 24, 2018. (Year: 2009).

Ettmayer, P., et al. "Lessons Learned from Marketed and Investigational Prodrugs." J. Med. Chem. (2004) 47(10), pp. 2393-2404.

Han, H. "Targeted Prodrug Design to Optimize Drug Delivery." AAPS Pharmsci. (2000), vol. 2 (1) article 6, pp. 1-11.

Handbook of Pharmaceutical Excipients, 2006 5th ed., edited by Raymond c Rowe et al., p. 185-187, 287-289, 466-470, 693-695, ISBN: 9780853696186.

Hendriks, R.W., etal. "Targeting Bruton's tyrosine kinase in B cell malignancies." Nature Reviews Cancer. (Apr. 2014), vol. 14, pp. 219-232. (Year: 2014).

International Search Report and Written Opinion dated Jun. 22, 2016 issued in International Patent Application No. PCT/US2016/026134.

Japanese Pharmaceutical Excipients Directory 2007, Yakuji Nippo, Limited, 2007, Vo.45, pp. 67-68, 79-80, 101, 146-147, 148, 214, 216, 226, 333.

Lymphoma Research Foundation. "Diffuse Large B-Cell Lymphoma (DLBCL)." copyright 2016. Available from: <http://www.lymphoma.org/site/pp.asp?c=bkLTKaOQLmK8E&b=6300153 >.

Matthews, et al.: Acute and Chronic Toxicity in Dogs, Rats, and Mice, Journal of the American Pharmaceutical Association, 1956, vol. XLV, No. 4, pp. 260-267.

Miles, R.R., et al. "Pediatric Diffuse Large B-cell Lymphoma Demonstrates A High Proliferation Index, Frequent c-Myc Protein Expression, and A High Incidence of Germinal Center Subtype." Pediatr Blood Cancer. (Sep. 2008). vol. 51, Issue 3, pp. 369-374. (Year: 2008).

Patil, P. S., et al. "Pharmaceutical Excipients: A review." International Journal of Advances in Pharmacy, Biology, and Chemistry. (Jan.-Mar. 2012), vol. 1, Issue 1, pp. 21-34. (Year: 2012).

Szakonyi, G., et al., "The effect of water on the solid state characteristics of pharmaceutical excipients: Molecular mechanisms, measurement techniques, and quality aspects of final dosage form", Int. j. Pharm. Investig.,Jan.-Mar. 2012, vol. 2, issue 1, pp. 18-25.

Testa, B. "Prodrug research: futile or fertile?" Biochem. Pharm. (2004) 68, pp. 2097-2106.

* cited by examiner

COMPOSITIONS CONTAINING IBRUTINIB

CROSS REFERENCE TO RELATED APPLICATIONS

This application is a continuation of U.S. patent application Ser. No. 17/706,783, filed Mar. 29, 2022, which is a continuation of U.S. patent application Ser. No. 16/708,929, filed Dec. 10, 2019, which is a continuation of U.S. patent application Ser. No. 15/602,989, filed May 23, 2017, which is a divisional of U.S. patent application Ser. No. 15/092,195 filed Apr. 6, 2016, which claims the benefit of U.S. Provisional Patent Application No. 62/143,659, filed Apr. 6, 2015, the entireties of the disclosure of which are incorporated by reference.

TECHNICAL FIELD

This invention relates to compositions containing Ibrutinib and methods for using same.

BACKGROUND

Targeted therapy involves identifying specific differences between cancer cells and normal cells. These differences are used to create a targeted therapy to attack the cancer cells without damaging the normal cells, thus leading to fewer side effects. Differences exist between the various types of targeted therapy but all interfere with the ability of the cancer cell to grow, divide, repair and/or communicate with other cells.

Ibrutinib is an anticancer drug targeting B-cell malignancies. Ibrutinib blocks signals that stimulate malignant B cells to grow and divide uncontrollably. It was approved by the US FDA in November 2013 for the treatment of mantle cell lymphoma and in February 2014 for the treatment of chronic lymphocytic leukemia. It is an orally-administered, selective and covalent inhibitor ($IC_{50}$=0.46 nM) of the enzyme Bruton's tyrosine kinase (BTK) via a covalent bond to the cysteine residue Cys-481 in the BTK active site. BTK is a signaling molecule of the B-cell antigen receptor (BCR) and cytokine receptor pathways. The BCR pathway is implicated in several B-cell malignancies, including MCL and B-cell CLL. Ibrutinib is marked in the US in oral capsule form (Imbruvica™)

What is needed in the art are alternate formulations containing Ibrutinib.

SUMMARY OF THE INVENTION

In one aspect, pharmaceutical compositions are provided comprising Ibrutinib, a salt, prodrug, or metabolite thereof, microcrystalline cellulose, croscarmellose sodium, sodium lauryl sulfate, and magnesium stearate. In one embodiment, the composition contains about 40 to about 45% by weight of Ibrutinib.

In another aspect, pharmaceutical compositions are provided comprising (i) about 40 to about 45% by weight of Ibrutinib; (ii) about 44 to about 47% by weight of microcrystalline cellulose; (iii) about 6 to about 8% by weight of croscarmellose sodium; (iv) about 1 to about 5% by weight of sodium lauryl sulfate; and (v) about 0.2 to about 0.3% by weight of magnesium stearate.

In a further aspect, pharmaceutical compositions are provided comprising (i) about 140 mg of Ibrutinib; (ii) about 151 mg of microcrystalline cellulose; (iii) about 23 mg of croscarmellose sodium; (iv) about 14 mg of sodium lauryl sulfate; and (v) about 1.6 mg of magnesium stearate.

In still another aspect, pharmaceutical compositions are provided comprising (i) about 50 mg of Ibrutinib; (ii) about 54 mg of microcrystalline cellulose; (iii) about 8 mg of croscarmellose sodium; (iv) about 5 mg of sodium lauryl sulfate; and (v) about 0.6 mg of magnesium stearate.

In yet a further aspect, capsules or sachets are provided comprising at least one of the pharmaceutical compositions described herein. In certain embodiments, the capsule is a standard or sprinkle.

In another aspect, pharmaceutical compositions are provided comprising Ibrutinib, a salt, prodrug, or metabolite thereof, microcrystalline cellulose, carboxymethylcellulose sodium, hydroxypropylmethylcellulose, citric acid monohydrate, disodium hydrogen phosphate, sucralose, sodium methyl parahydroxybenzoate, sodium ethyl parahydroxybenzoate, concentrated hydrochloric acid, sodium hydroxide, and water.

In still a further aspect, pharmaceutical compositions are provided comprising (i) about 70 mg/mL of Ibrutinib; (ii) about 13 mg/mL of a combination of microcrystalline cellulose and carboxymethylcellulose sodium; (iii) about 2.5 mg/mL of hydroxypropylmethylcellulose; (iv) about 1.5 mg/mL of citric acid monohydrate; (v) about 1.4 mg/mL of disodium hydrogen phosphate; (vi) about 1 mg/mL of sucralose; (vii) about 1 mg/mL of sodium methyl parahydroxybenzoate; and (viii) about 0.6 mg/mL of sodium ethyl parahydroxybenzoate.

In other aspects, pharmaceutical compositions are provided comprising (i) about 40 mg/mL of Ibrutinib; (ii) about 14 mg/mL of a combination of microcrystalline cellulose and carboxymethylcellulose sodium; (iii) about 1 mg/mL of hydroxypropylmethylcellulose; (iv) about 1.5 mg/mL of citric acid monohydrate; (v) about 1.4 mg/mL of disodium hydrogen phosphate; (vi) about 0.5 mg/mL of sucralose; (vii) about 1.4 mg/mL of sodium methyl parahydroxybenzoate; and (viii) about 0.6 mg/mL of sodium ethyl parahydroxybenzoate.

In yet another aspect, methods for treating a B-cell proliferative disorder are provided comprising the steps of administering at least one pharmaceutical composition described herein to a subject in need thereof. In certain embodiments, the B-cell proliferative disorder is a non-Hodgkin lymphoma, Waldenstrom macroglobulinemia, plasma cell myeloma, or chronic lymphocytic leukemia.

In a further aspect, methods for treating a lymphoma are provided comprising administering at least one composition described herein to a subject in need thereof.

In another aspect, methods of treating a leukemia are provided comprising administering at least one composition described herein to a subject in need thereof.

In still a further aspect, methods for treating mantle cell lymphoma in a subject who has already received at least one prior therapy for mantle cell lymphoma are provided comprising administering at least one composition described herein to the subject once per day.

In a further aspect, the treatment methods herein involve use of a sprinkle capsule that is open to facilitate sprinkling of the capsule's contents into food or a beverage. In one embodiment, the beverage is water. In another embodiment, the food is a soft food. Capsule contents can also be administered via feeding tube after spending into suitable vehicle such as water, milk or other common beverages. Please note the suspension formulation can also be administered via feeding tube.

In yet another aspect, processes for preparing compositions described herein are provided comprising (a) blending microcrystalline cellulose, a first portion of sodium lauryl sulfate, and a first portion of croscarmellose sodium; (b) blending the product of step (a) with a first portion of Ibrutinib; (c) blending the product of step (b) with a second portion of Ibrutinib; (d) blending the product of step (c) with a first portion of magnesium stearate; (e) roller compacting the product of step (d); (f) milling the ribbons produced in step (e); (g) blending the granules produced in step (e) with a second portion of sodium lauryl sulfate and croscarmellose sodium; and (h) blending the product of step (g) with a second portion of magnesium stearate. In one embodiment, the process further includes (i) adding the product of step (h) to a capsule.

In a further aspect, processes for preparing compositions described herein are provided comprising (a) mixing water, microcrystalline cellulose croscarmellose sodium; (b) mixing water with hydroxypropylmethylcellulose; (c) mixing the product of step (b) with Ibrutinib; (d) mixing the product of steps (a) and (c); (e) mixing the product of the step (d) with sucralose; (f) mixing the product of step (e) with sodium methyl parahydroxybenzoate and sodium ethyl parahydroxybenzoate; (g) mixing the product of step (f) with monohydrate citric acid; and (h) mixing the product of step (g) with anhydrous disodium hydrogen phosphate. In one embodiment, the process further includes (i) adjusting the pH of the product of step (h) to a pH of about 6. In another embodiment, the processes further include adding water to the product of step (h) or (i). In a further aspect, the processes further include adding the composition to a vial.

Other aspects and advantages of the present invention are described further in the following detailed description of the preferred embodiments thereof.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific compositions, methods, devices, and systems disclosed. In addition, the drawings are not necessarily drawn to scale.

DETAILED DESCRIPTION OF THE ILLUSTRATIVE EMBODIMENTS

Figure 1:
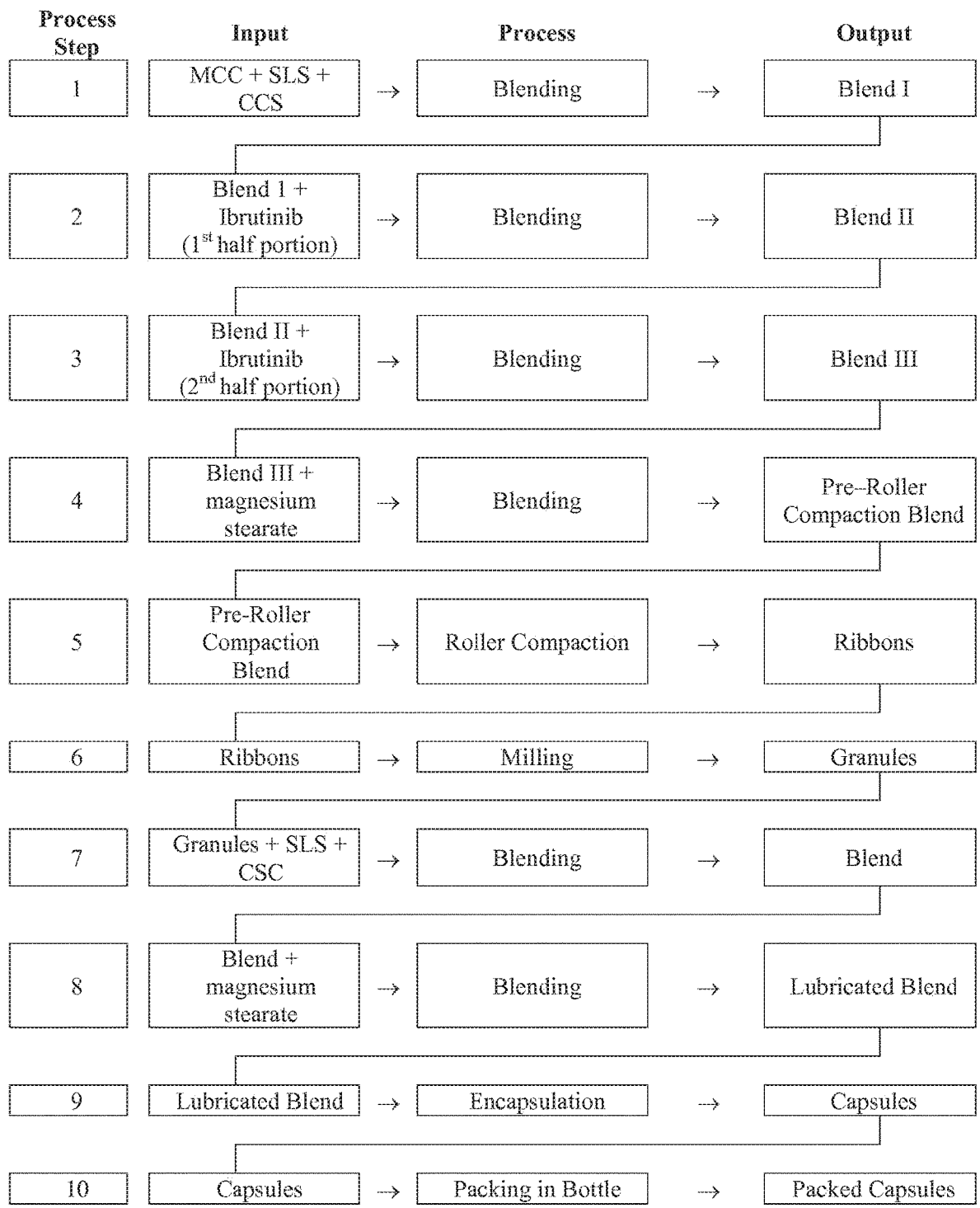
FIG. 1 provides a process flow diagram for preparing capsules containing Ibrutinib.
Figure 2:
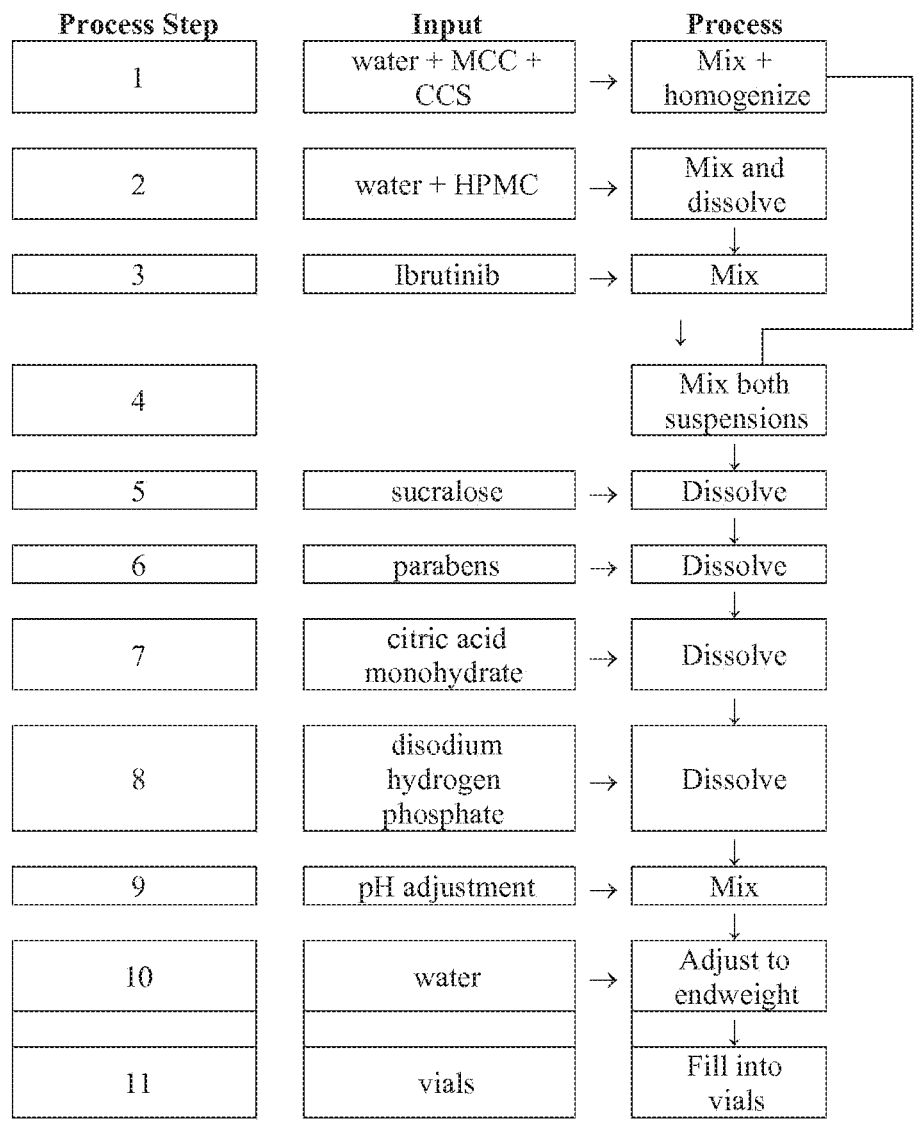
FIG. 2 provides a process flow diagram for preparing liquid formulations containing Ibrutinib.

The present invention may be understood more readily by reference to the following description taken in connection with the accompanying Figures and Examples, all of which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to the features and methods of making and using the compositions described herein.

In the present disclosure the singular forms "a", "an" and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" or "substantially" it will be understood that the particular value forms another embodiment. In general, use of the term "about" or "substantially" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about" or "substantially". In other cases, the gradations used in a series of values may be used to determine the intended range available to the term "about" or "substantially" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

The term "subject" as used herein refers to an animal being treated for a condition requiring Ibrutinib. In one embodiment, the subject is a human. In another embodiment, the subject is an adult, including a young adult, mature adult, or elderly adult, or child, including a teenager.

The term "purified" as used herein preferably refers to Ibrutinib that contains less than about 1% impurities. In one embodiment, the Ibrutinib contains less than about 0.5% impurities. In another embodiment, the Ibrutinib contains less than about 0.1% impurities. In a further embodiment, the Ibrutinib is about 100% pure.

The terms intragranular and extragranular as used herein are known in the art of formulations. An intragranular form of a formulation component is added before granule formation. Similarly, an extragranular form of a formulation component is added to the granules of the formulation prior to compression. Simply stated, the extragranular portion breaks the composition into granules and the intragranular portion disintegrates the granules to release the Ibrutinib, a salt, prodrug, or metabolite thereof.

Abbreviations used herein include CCS (croscarmellose sodium), MCC (microcrystalline cellulose), SLS (sodium lauryl sulfate), HPMC (hydroxypropylmethylcellulose; hypromellose), DSC (differential scanning calorimeter), BHT (butylated hydroxytoluene), BHA (butylated hydroxyanisole), sodium methyl parahydroxybenzoate, sodium ethyl, CLL (chronic lymphocytic leukemia), and SLL (small lymphocytic lymphoma).

A. Ibrutinib Form

The compositions described herein contain Ibrutinib (Imbruvica) as the active agent. Ibrutinib is described and may be prepared as set forth in U.S. Pat. Nos. 7,514,444; 8,003,309; 8,697,711; 8,735,403; 8,957,079; and 8,754,091, which are incorporated by reference. As known in the art, Ibrutinib is 1-[(3R)-3-[4-amino-3-(4-phenoxyphenyl)-1H-pyrazolo[3,4 d]pyrimidin-1-yl]-1-piperidinyl]-2-propen-1-one and has the following structure. Ibrutinib has a melting point range of about 149° C. to about 158° C., a partition coefficient of about 4 at a pH of about 7, a dissociation constant of about 3.7, and a DSC melting point initiating at about 156° C.

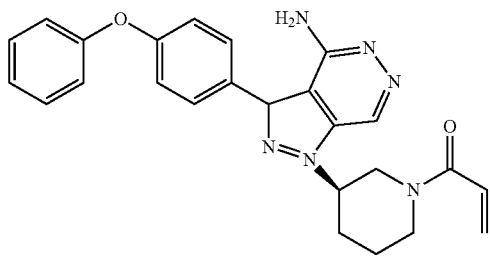

The Ibrutinib utilized herein may include other forms, including metabolites thereof, provided that the Ibrutinib form is stable and non-toxic. The Ibrutinib form may also have some or the same activity as the base Ibrutinib molecule. In one embodiment, an active metabolite of Ibrutinib is of the following structure.

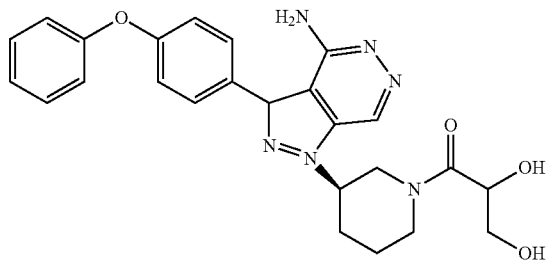

The Ibrutinib form utilized herein may encompass tautomeric forms of Ibrutinib, prodrugs and salts. In one embodiment, the Ibrutinib salts may be derived from pharmaceutically or physiologically acceptable acids, bases, alkali metals and alkaline earth metals. Physiologically acceptable acids include those from inorganic and organic acids. Inorganic acids are known in the art and include, without limitation, hydrochloric, hydrobromic, hydroiodic, sulfuric, nitric, and phosphoric acids. Organic acids are also known in the art and include, without limitation, lactic, formic, acetic, fumaric, citric, propionic, oxalic, succinic, glycolic, glucuronic, maleic, furoic, glutamic, benzoic, anthranilic, salicylic, tartaric, malonic, mallic, phenylacetic, mandelic, embonic, methanesulfonic, ethanesulfonic, panthenoic, benzenesulfonic, toluenesulfonic, stearic, sulfanilic, alginic, and galacturonic acids. Inorganic bases are known in the art and include, without limitation, aluminum, calcium, lithium, magnesium, potassium, sodium, and zinc sulfate or phosphates. Similarly, organic bases are known in the art and include, without limitation, N,N-dibenzylethylenediamine, chloroprocaine, choline, diethanolamine, ethylenediamine, meglumine, and procaine. Alkali salts and alkaline earth metal salts can include, without limitation, sodium, potassium, calcium and magnesium salts in the form of esters, and carbamates.

Prodrugs of Ibrutinib are also contemplated and include, without limitation, esters, carbamates, sulfates, ethers, oximes, carbonates, among others. The prodrug forms, which, when administered in such form, convert to the active moiety in vivo. See, Testa, "Prodrugs Revisited: The "Ad Hoc" Approach as a Complement to Ligand Design", Medicinal Research Reviews, 16(3):233-241, ed., John Wiley & Sons (1996), which is incorporated by reference.

A "metabolite" of Ibrutinib may also be utilized as described herein. As known in the art, a metabolite is a compound of Ibrutinib formed when the compound is metabolized as described in "The Pharmacological Basis of Therapeutics," 9th Edition, McGraw-Hill (1996), which is incorporated by reference.

B. Solid Formulations

Ibrutinib may be formulated in solid formulations for administration to a subject. The solid formulation is substantially dry, i.e., free from liquid. In one embodiment, the solid formulation is about 90% or greater dry.

In one embodiment, a pharmaceutical composition discussed herein contains Ibrutinib, a salt, prodrug, or metabolite thereof, microcrystalline cellulose, croscarmellose sodium, sodium lauryl sulfate, and magnesium stearate. As noted above, the Ibrutinib contained in this composition may be the base molecule, salt, prodrug, or metabolite thereof.

The composition contains about 40 to about 45% by weight of Ibrutinib, a salt, prodrug, or metabolite thereof. In one embodiment, the composition contains about 41 to about 44% by weight of Ibrutinib, a salt, prodrug, or metabolite thereof. In a further embodiment, the composition contains about 42 to about 43% by weight of Ibrutinib, a salt, prodrug, or metabolite thereof. In another embodiment, the composition contains about 42 or about 43% by weight of Ibrutinib, a salt, prodrug, or metabolite thereof. In yet a further embodiment, the composition contains about 50 to about 140 mg of Ibrutinib, a salt, prodrug, or metabolite thereof. In still another embodiment, the composition contains about 50 mg of Ibrutinib, a salt, prodrug, or metabolite thereof.

One or more suspending agent may be included in the liquid composition discussed herein. In one embodiment, microcrystalline cellulose is also included in the compositions described herein. In further embodiments, the composition contains about 44 to about 47% by weight of microcrystalline cellulose. In another embodiment, the composition contains about 45 to about 46% by weight of microcrystalline cellulose.

The compositions may also contain croscarmellose sodium. The croscarmellose sodium may be in an intragranular or extragranular form. In one embodiment, the composition contains about 6 to about 8% by weight of croscarmellose sodium. In another embodiment, the composition contains about 7% by weight of croscarmellose sodium. In a further embodiment, the composition contains about 3 to about 5% by weight of intragranular croscarmellose sodium. In yet another embodiment, the composition contains about 4% by weight of intragranular croscarmellose sodium. In still a further embodiment, the composition contains about 2 to about 4% by weight of extragranular croscarmellose sodium. In another embodiment, the composition contains about 3% by weight of croscarmellose sodium. In a further embodiment, the composition contains about 13 mg of intragranular croscarmellose sodium and about 9.9 mg of extragranular croscarmellose sodium. In a further embodiment, the composition contains about 4.6 mg of intragranular croscarmellose sodium and about 3.5 mg of extragranular croscarmellose sodium.

Sodium lauryl sulfate may also be included in the compositions discussed herein. The sodium lauryl sulfate may be in intragranular and/or extragranular forms. In one embodiment, the composition contains about 1 to about 5% by weight of sodium lauryl sulfate. In another embodiment, the composition contains about 2 to about 4.5% by weight of sodium lauryl sulfate. In a further embodiment, the composition contains about 3 to about 4% by weight of sodium lauryl sulfate. In still another embodiment, the composition contains about 2.5 to about 3% by weight of intragranular sodium lauryl sulfate. In yet a further embodiment, the composition contains about 3% by weight of intragranular sodium lauryl sulfate. In another embodiment, the composition contains about 1 to about 2% by weight of extragranular sodium lauryl sulfate. In still a further embodiment, the composition contains about 1.4% by weight of extragranular sodium lauryl sulfate. In yet another embodiment, the composition contains about 9.4 mg of intragranular sodium lauryl sulfate and about 4.6 mg of extragranular sodium lauryl sulfate. In a further embodiment, the composition contains about 3.3 mg of intragranular sodium lauryl sulfate and about 1.6 mg of extragranular sodium lauryl sulfate.

The compositions described herein may also contain magnesium stearate. The magnesium stearate may be in intragranular and/or extragranular forms. In one embodiment, the composition contains about 0.4 to about 0.6% by weight of magnesium stearate. In another embodiment, the composition contains about 0.4 to about 0.5% by weight of magnesium stearate. In another embodiment, the composition contains about 0.45 to about 0.5% by weight of magnesium stearate. In a further embodiment, the composition contains about 0.2 to about 0.3% by weight of intragranular magnesium stearate. In still another embodiment, the composition contains about 0.2 to about 0.3% by weight of extragranular magnesium stearate. In yet a further embodiment, the composition contains about 0.8 mg of intragranular magnesium stearate and about 0.8 mg of extragranular magnesium stearate. In another embodiment, the composition contains about 0.3 mg of intragranular magnesium stearate and about 0.3 mg of extragranular magnesium stearate.

In one embodiment, a pharmaceutical composition is described herein and includes an intragranulation containing Ibrutinib, a salt, prodrug, or metabolite thereof, microcrystalline cellulose, croscarmellose sodium, sodium lauryl sulfate, and magnesium stearate.

In another embodiment, the pharmaceutical composition includes an extragranulation containing croscarmellose sodium, sodium lauryl sulfate, and magnesium stearate.

In a further embodiment, a pharmaceutical composition is provided and contains (i) about 40 to about 45% by weight of Ibrutinib; (ii) about 44 to about 47% by weight of microcrystalline cellulose; (iii) about 6 to about 8% by weight of croscarmellose sodium; (iv) about 1 to about 5% by weight of sodium lauryl sulfate; and (v) about 0.2 to about 0.3% by weight of magnesium stearate.

In still another embodiment, a pharmaceutical composition is provided and contains (i) about 140 mg of Ibrutinib; (ii) about 151 mg of microcrystalline cellulose; (iii) about 23 mg of croscarmellose sodium; (iv) about 14 mg of sodium lauryl sulfate; and (v) about 1.6 mg of magnesium stearate.

In yet a further embodiment, a pharmaceutical composition is provided and contains (i) about 50 mg of Ibrutinib; (ii) about 54 mg of microcrystalline cellulose; (iii) about 8 mg of croscarmellose sodium; (iv) about 5 mg of sodium lauryl sulfate; and (v) about 0.6 mg of magnesium stearate.

In another embodiment, pharmaceutical compositions containing the components of Table 1 are provided.

TABLE 1

| Ingredient | Amount (mg) 140 mg capsule | Amount (mg) 50 mg capsule |
|---|---|---|
| Intragranular | | |
| Ibrutinib, micronized (Lonza, Nansha) | 140.00 | 50.00 |
| Microcrystalline Cellulose (Avicel PH 101) | 151.40 | 54.07 |
| Croscarmellose Sodium (Ac-di-sol) | 13.10 | 4.68 |
| Sodium lauryl Sulfate (Kolliphor SLS fine) | 9.40 | 3.36 |
| Magnesium Stearate (Non-Bovine #5712) | 0.80 | 0.29 |
| Extragranular | | |
| Croscarmellose Sodium (Ac-di-sol) | 9.90 | 3.54 |
| Sodium lauryl Sulfate (Kolliphor SLS fine) | 4.60 | 1.64 |
| Magnesium Stearate (Non-Bovine #5712) | 0.80 | 0.29 |
| Total fill weight | 330.00 | 117.87 |
| Hard Gelatin Capsule size 0 | 1 | 1 |

The solid compositions described herein contain particles of an optimal size to permit dissolution of the composition, e.g., the particles are less than or equal to about 10 μ. The sizes of the particles of the composition may be measured by passing the solid composition through screens of varying sizes. If the particles of the composition are larger than the optimal size and if the same have not yet been encapsulated in a capsule or dissolved in one or more excipient, the same can be subject to further milling and screening steps, among others, to reduce the particle size. Ibrutinib may optionally be micronized under nitrogen and conventional micronizing techniques, for example with a Trost or jet mill, applied to non-micronized Ibrutinib. However, the compositions described herein are not limited to the method by which the Ibrutinib is produced. Ibrutinib may have a median particle size of less than about 10 μm, less than about 7 μm, or than about 5 μm. Specifically, 90% of the particles are less than or equal to about 10 μm and 50% are less than or equal to about 10 μm as determined by the Malvern method, which is readily understood by one of skill in the art.

A variety of equipment may be utilized to perform the manufacturing processes of preparing the solid compositions and includes bags of small, medium, and large sizes, screens of varying sizes, and blenders. The process may also include mixing, extruding, fusing, compacting and/or milling of the composition, typically using compactors and mills selected by those skilled in the art. The milling step may be performed on particles of varying sizes, i.e., large particles, powders, and fine powders to obtain a more uniform particle size. The milling may include one or more separating, recycling, and screening steps to obtain the desired particle sizes. In one embodiment, the compositions may be prepared by dry mixing Ibrutinib, based upon the total weight of the composition, with the other components of the composition. In another embodiment, the compositions described herein are prepared by wet mixing Ibrutinib, based upon the total weight of the composition, with the other components of the composition. Drying may be performed using drying instruments selected by one of skill in the art. See. e.g., Lachman, "The Theory and Practice of Industrial Pharmacy", $3^{rd}$ ed. (1986), which is incorporated by reference.

In one embodiment, the solid compositions discussed herein are prepared by (a) blending microcrystalline cellulose, a first portion of sodium lauryl sulfate, and a first portion of croscarmellose sodium; (b) blending the product of step (a) with a first portion of Ibrutinib; (c) blending the product of step (b) with a second portion of Ibrutinib; (d) blending the product of step (c) with a first portion of magnesium stearate; (e) roller compacting the product of step (d); (f) milling the ribbons produced in step (e); (g) blending the granules produced in step (f) with a second portion of sodium lauryl sulfate and croscarmellose sodium; and (h) blending the product of step (g) with a second portion of magnesium stearate. In another embodiment, the solid compositions are prepared as described in FIG. 1.

The solid compositions may then be formed into a suitable dosing unit for delivery to a patient as determined by one skilled in the art. Suitable dosing units include oral dosing units. In one embodiment, the composition is added to a capsule. In a further embodiment, the capsule is for pediatric administration. In yet another embodiment, the capsule is for administration by an adult who is incapable of swallowing a solid drug formulation. In another embodiment, the capsule is a HPMC (hypromellose) capsule. In yet a further embodiment, the capsule is a gelatin capsule. In still another embodiment, the capsule is a hard gelatin capsule. In still another embodiment, the capsule is a standard or sprinkle capsule. In a further embodiment, the capsule is a Swedish orange capsule. In another embodiment, the capsule is a size 0 capsule. In yet another embodiment, the sprinkle capsule may be opened and the contents added to a substance such as a food or drink which may be ingested by the subject. The food may be a semi-solid or a solid, including soft food.

In another embodiment the capsules containing Ibrutinib are film-coated. Suitable film-coatings are known to those of skill in the art. For example, the film-coating may be a polymer such as HPMC, ethyl cellulose, polyvinyl alcohol, or combinations thereof.

The solid compositions may also be added to a sachet. The term "sachet" as used herein refers to a bag or case which is capable of holding a composition described herein. The size of the sachet depends on the amount of the composition to be added. In one embodiment, the sachet is a single dose sachet. In another embodiment, the sachet contains a bulk amount of the compositions described herein. In the latter case, the patient, physician, or caretaker measures the appropriate dosage of the compositions for administration. In a further embodiment, the sachet is a paper/aluminum/polyethylene laminate or polyester/aluminum/polyethylene laminate, both of which may optionally be located with a barrier coating such as ethylenevinyl acetate, polyvinyl acetate, polysiloxane, or melamine, among others. In another embodiment, the sachet may be opened and the contents added to a substance such as a food or drink which may be ingested by the subject. The drink may include, without limitation, water, milk, or other common beverages.

The liquid formulation of solid composition (formulated in a liquid) may be administered to a subject via a feeding tube. The feeding tube may be temporarily or permanently affixed to a patient using skill in the art. The patient may be conscious, semi-conscious, or asleep, depending on the need as determined by the attending physician. Several types of feeding tubes are known in the art and may be selected by the attending physician.

C. Liquid Formulation

Ibrutinib may be also formulated in liquid formulations for administration to a subject. Liquids include, without limitation, suspensions, syrups, and elixirs. These dosing units are readily prepared using the methods described herein and those known to those of skill in the art. When formulated as suspension, particle settling may occur, thereby requiring resuspending particles in the suspension using skill in the art.

The liquid compositions described herein contain Ibrutinib, a salt, prodrug, or metabolite thereof, microcrystalline cellulose, carboxymethylcellulose sodium, hydroxypropylmethylcellulose, citric acid monohydrate, disodium hydrogen phosphate, sucralose, sodium methyl parahydroxybenzoate, sodium ethyl parahydroxybenzoate, concentrated hydrochloric acid, sodium hydroxide, and water.

Accordingly, the liquid composition contains about 30 to about 80 mg/mL of Ibrutinib, a salt, prodrug, or metabolite thereof. In some embodiments, the composition contains about 30 to about 50 mg/mL of Ibrutinib, a salt, prodrug, or metabolite thereof. In further embodiments, the composition contains about 40 mg/mL of Ibrutinib, a salt, prodrug, or metabolite thereof. In other embodiments, the composition contains about 60 to about 80 mg/mL to about 70 mg/mL of Ibrutinib, a salt, prodrug, or metabolite thereof. In yet further embodiments, the composition contains about 70 mg/mL of Ibrutinib, a salt, prodrug, or metabolite thereof.

One or more suspending agent may be included in the liquid composition discussed herein. In one embodiment, microcrystalline cellulose and carboxymethylcellulose sodium may also be included in the liquid composition. In some embodiments, the composition contains about 12 to about 15 mg/mL of the suspending agent. In further embodiments, the composition contains about 13 to about 15 mg/mL of suspending agent. In other embodiments, the composition contains about 12 to about 14 mg/mL of the suspending agent. In a further embodiment, the composition contains about 13 mg/mL of the suspending agent. In another embodiment, the composition contains about 14 mg/mL of the suspending agent.

The composition may also contain one or more of a wetting agent. In one embodiment, the composition contains hydroxypropylmethylcellulose. In some embodiments, the composition contains about 0.5 to about 3 mg/mL of the wetting agent. In other embodiments, the composition contains about 2 to about 3 mg/mL of the wetting agent. In another embodiment, the composition contains about 2.5 mg/mL of the wetting agent. In further embodiments, the composition contains about 0.5 to about 1.5 mg/mL of the wetting agent. In yet other embodiments, the composition contains about 1 mg/mL of the wetting agent.

One or more buffering agent may be included in the composition, solid or liquid. In one embodiment, the buffering agent is citric acid monohydrate or disodium hydrogen phosphate. In another embodiment, the composition contains about 2.5 to about 3.5 mg/mL of a buffering agent. In some embodiments, the composition contains about 1 to about 1.5 mg/mL of a first buffering agent. In other embodiments, the composition contains about 0.5 to about 0.7 mg/mL of the buffering agent. In a further embodiment, the composition contains about 1.5 mg/mL of a first buffering agent and about 1.5 mg/mL of a second buffering agent. In other embodiments, the composition contains about 1.6 mg/mL of a first buffering agent and about 1.4 mg/mL of a second buffering agent. In yet another embodiment, the composition contains about 1.5 mg/mL or 1.6 mg/mL of citric acid monohydrate. In still a further embodiment, the composition contains about 1.4 mg/mL of disodium hydrogen phosphate.

Sweeteners may also be included in the compositions, solid or liquid, described herein. In one embodiment, the sweeter is sucralose. In another embodiment, the composition contains about 0.1 to about 1.5 mg/mL of the sweetener. In other embodiments, the composition contains 0.5 to about 1.5 mg/mL of the sweetener. In a further embodiment, the composition contains about 1 mg/mL of the sweetener. In another embodiment, the composition contains about 0.5 mg/mL of the sweetener.

One or more of a preservative may further be included in the compositions, solid or liquid. The preservative desirably provides an optimal microbiological activity in the liquid formulation. In one embodiment, the composition retains the optimal activity of the methyl/ethyl parabens. In one embodiment, the preservative is sodium methyl parahydroxybenzoate. In another embodiment, the preservative is sodium ethyl parahydroxybenzoate. In a further embodiment, the composition contains about 1.5 to about 2.5 mg/mL of the preservative. In other embodiments, the composition contains about 1.5 to about 2 mg/mL of the preservative. In a further embodiment, the composition contains about 0.5 to about 1.8 mg/mL of a first preservative. In yet another embodiment, the composition contains about 1.0 to about 1.8 mg/mL of a first preservative. In still a further embodiment, the composition contains about 1.25 to about 1.5 mg/mL of a second preservative. In another embodiment, the composition contains about 1.1 mg/mL of a first preservative and about 0.6 mg/mL of a second preservative. In other embodiments, the composition contains about 1.4 mg/mL of a first preservative and about 0.7 mg/mL of a second preservative. In yet a further embodiment, the composition contains about 1 mg/mL of sodium methyl parahydroxybenzoate. In still another embodiment, the composition contains about 0.6 mg/mL of sodium ethyl parahydroxybenzoate. In further embodiments, the composition contains about 1.4 mg/mL of sodium methyl parahydroxybenzoate. In still another embodiment, the composition contains about 0.7 mg/mL of sodium ethyl parahydroxybenzoate.

If the pH of the solution requires adjustment, a pH adjustor may be included in the composition. One of skill in the art would be able select suitable pH adjustor to ensure a safe, stable and subject-compatible composition. In one embodiment, the pH of the composition is adjusted to about 6. In another embodiment, the pH adjustor is an acid or base. In a further embodiment, the pH adjustor is hydrochloric acid. In still another embodiment, the pH adjustor is concentrated hydrochloric acid. In yet further embodiment the pH adjustor is sodium hydroxide.

Finally, a sufficient amount of a diluent, such as water, may be included in the composition to ensure a volume of about 1 mL. In one embodiment, the diluent is purified water. Compositions containing lesser amounts of Ibrutinib can prepared as described herein by diluting compositions containing greater amounts of Ibrutinib using the diluent.

In one embodiment, a pharmaceutical composition is provided and contains (i) about 70 mg/mL of Ibrutinib; (ii) about 13 mg/mL of microcrystalline cellulose and carboxymethylcellulose sodium; (iii) about 2.5 mg/mL of hydroxypropylmethylcellulose; (iv) about 1.5 mg/mL of citric acid monohydrate; (v) about 1.4 mg/mL of disodium hydrogen phosphate; (vi) about 1 mg/mL of sucralose; (vii) about 1 mg/mL of sodium methyl parahydroxybenzoate; and (viii) about 0.6 mg/mL of sodium ethyl parahydroxybenzoate.

In another embodiment, a pharmaceutical composition is provided and contains the components of Table 2.

TABLE 2

| Component | Concentration (mg/mL) |
| --- | --- |
| Ibrutinib micronized | 70 |
| MCC and CMC | 13 |
| HPMC | 2.5 |
| Citric acid monohydrate | 1.513 |
| Disodium hydrogen phosphate | 1.38 |
| Sucralose | 1 |
| Sodium methyl parahydroxybenzoate | 1.145 |
| Sodium ethyl parahydroxybenzoate | 0.575 |

In other embodiments, a pharmaceutical composition is provided and contains (i) about 40 mg/mL of Ibrutinib; (ii) about 14 mg/mL of microcrystalline cellulose and carboxymethylcellulose sodium; (iii) about 1 mg/mL of hydroxypropylmethylcellulose; (iv) about 1.6 mg/mL of citric acid monohydrate; (v) about 1.4 mg/mL of disodium hydrogen phosphate; (vi) about 0.5 mg/mL of sucralose; (vii) about 1.4 mg/mL of sodium methyl parahydroxybenzoate; and (viii) about 0.7 mg/mL of sodium ethyl parahydroxybenzoate.

In further embodiments, a pharmaceutical composition is provided and contains the components of Table 3.

TABLE 3

| Component | Concentration (mg/mL) |
| --- | --- |
| Ibrutinib micronized | 40 |
| MCC and CMC | 14 |
| HPMC | 1 |
| Citric acid monohydrate | 1.602 |
| Disodium hydrogen phosphate | 1.38 |
| Sucralose | 0.5 |
| Sodium methyl parahydroxybenzoate | 1.3582 |
| Sodium ethyl parahydroxybenzoate | 0.6773 |

The liquid compositions may be prepared by (a) mixing water, microcrystalline cellulose croscarmellose sodium; (b) mixing water with hydroxypropylmethylcellulose; (c) mixing the product of step (b) with Ibrutinib; (d) mixing the product of steps (a) and (c); (e) mixing the product of step (d) with sucralose; (f) mixing the product of step (e) with sodium methyl parahydroxybenzoate and sodium ethyl parahydroxybenzoate; (g) mixing the product of step (f) with monohydrate citric acid; and (h) mixing the product of step (g) with anhydrous disodium hydrogen phosphate. The process my further include (i) adjusting the pH of the product of step (h) to a pH of about 6. In one embodiment, step (i) is performed using hydrochloric acid or sodium hydroxide. The process may also include adding water to the product of step (h) or (i). It is also envisioned that the product of step (a) may be homogenized using skill known in the art.

Liquid formulations may then be stored as a bulk unit or distributed into separate, smaller vials for storage or purchasing by the customer. One of skill in the art would readily be able to select suitable vials for use herein. In one embodiment, the liquid composition is added to a vial. In a further embodiment, the vial is glass. In another embodiment, the vial is clear or amber. In a further embodiment, the vial may be sealed. In yet another embodiment, the vial is sealed with a rubber stopper. In a further embodiment, the vial is sealed with a Teflon coated rubber stopper. The stopper optionally contains a removable, i.e., tearable, aluminum cap. In still another embodiment, the vial is a 10 mL/20 mm vial. In yet a further embodiment, the vial is a drinking vial.

Additionally, the drug product will be administered as mono dose to each subject after a suitable sample shaking to resuspend particles before administration. Furthermore, after drug product administration, vial will be rinsed with an adequate amount of water and the entire contents of the vial will be administered to subject. For reasons mentioned above, even if settling happens, it is not expected to have an effect on the delivered dose.

D. Additional Components

Other components can be added to the compositions described herein as determined by one of skill in the art. The additional components may be inert and do not interfere with the function of the required components of the compositions. The compositions may, therefore, include other adjuvants, syrups, elixirs, diluents, binders, lubricants, surfactants, granulating agents, disintegrating agents, emollients, metal chelators, pH adjustors, coloring preservatives, antioxidants, agents, surfactants, fillers, disintegrants, or combinations thereof.

Preservatives may include ascorbic acid, BHT and BHA, sodium methyl parahydroxybenzoate, sodium ethyl parahydroxybenzoate, or combinations thereof.

Sweeteners such as natural or artificial sweeteners, or a combination thereof, may be included in the compositions described herein. In one embodiment, the natural sweetener is sucrose including raw sugar, granulated sugar, brown sugar, confectioner's sugar, and turbinado sugar, fructose, honey, fruit sugar, high fructose corn syrup, corn syrup, sugar alcohols such as mannitol, sorbitol, xylitol, erythritol, hydrogenated starch hydrolysate, lactitol, or maltitol, osmalt, dextrose, invert sugar, agave nectar, glucose, lactose, maltose, maple sugar, date sugar, molasses, stevia extract, tagatose, trehalose, or any combinations thereof. Another embodiment, the artificial sweetener is sucralose, aspartame, saccharine, neotame, advantame, or acesulfame potassium. In still a further embodiment, sugar may be included in the compositions.

Binders may include, without limitation, cellulose, methylcellulose, hydroxymethylcellulose, carboxymethylcellulose calcium, carboxymethylcellulose sodium, hydroxypropylcellulose, hydroxypropylmethylcellulose phthalate, noncrystalline cellulose, polypropylpyrrolidone, polyvinylpyrrolidone (povidone, PVP), gelatin, gum arabic and acacia, polyethylene glycols, starch, sugars such as sucrose, kaolin, dextrose, and lactose, cholesterol, tragacanth, stearic acid, gelatin, casein, lecithin (phosphatides), cetostearyl alcohol, cetyl alcohol, cetyl esters wax, dextrates, dextrin, glyceryl monooleate, glyceryl monostearate, glyceryl palmitostearate, polyoxyethylene alkyl ethers, polyoxyethylene castor oil derivatives, polyoxyethylene stearates, polyvinyl alcohol, and gelatin, among others.

Lubricants may include anhydrous silicic acid, talc, stearic acid, sodium lauryl sulfate, magnesium stearate and sodium stearyl fumarate, among others.

Granulating agents may include, without limitation, silicon dioxide, starch, calcium carbonate, pectin, crospovidone, and polyplasdone.

Disintegrating agents or disintegrants may include, without limitation, starch, carboxymethylcellulose, substituted hydroxypropylcellulose, sodium bicarbonate, calcium phosphate, calcium citrate, sodium starch glycolate, pregelatinized starch or crospovidone.

Emollients may include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

Surfactants may include, without limitation, polysorbates, sorbitan esters, poloxamer, or sodium lauryl sulfate.

Metal chelators may include, without limitation, physiologically acceptable chelating agents including edetic acid, malic acid, or fumaric acid.

The compositions described herein, in dry or liquid form, have a pH of about 5.5 to about 6.5. pH adjusters may be utilized to adjust the pH of a solution containing Ibrutinib to about 6. pH adjustors may include, without limitation, citric acid, ascorbic acid, fumaric acid, malic acid, hydrochloric acid, sodium hydroxide, salts thereof, or combinations thereof.

E. Stability of the Compositions

The Ibrutinib compositions as described herein, whether in solid or liquid form, are stable under neutral conditions, i.e., a pH of about 6 to about 8. The compositions are also stable under light irradiation. In one embodiment, the compositions are stable over a period of about 1 month for samples stored at varying temperatures and humidities. The term stable as used herein refers to the compositions described herein which degrade less than about 3%. In one embodiment, the compositions are stable at about 20° C./50% relative humidity to about 45° C./75% relative humidity. In another embodiment, the compositions described herein degrade less than about 3% over a period of greater than 1 month at temperatures at or greater than about 25° C. and a relative humidity at or greater than about 60%.

The solid compositions are also stable for at least about 6 hours when combined with an agent that is semi-solid or liquid. In one embodiment, the solid compositions may be suspended in a liquid or semi-solid and re-dispersed after 6 hours. In another embodiment, the solid compositions suspended in a liquid or semi-solid are stable for up to about 6 hours.

Stability may be monitored by a number of methods known in the art. In one embodiment, the capsules and liquids may be observed to detect any physical aspect or color change. In one embodiment, a capsule color change or deformation of the capsule may indicate degradation or deterioration of capsule and thus affect safety or efficacy.

The compositions described herein may be stored at reduced, room, or elected temperatures. In one embodiment, the compositions are stored at temperatures of about 0 to about 10° C. In another embodiment, the compositions are stored at temperatures of about 2 to about 8° C. The compositions may be stored in the absence of water, air, and moisture. However, storage at room temperature, among other atmospheric conditions, does not affect the overall stability of the compositions.

F. Methods of Using the Compositions

Also provided are method of delivering Ibrutinib to a patient, where the method includes administering a composition described herein to a patient. The compositions are thereby useful in treating or preventing conditions. In some embodiments, the conditions are those recited in U.S. Pat. Nos. 8,497,277; 8,476,284; 8,703,780; and 8,754,090, which are incorporated by reference herein.

The compositions are useful in therapeutically treating a subject having one or more of any of the conditions noted herein. The compositions may also be prophylactically useful, i.e., the compositions may be administered to a patient susceptible to or otherwise at risk of developing a malignancy. The compositions may further be used in maintenance therapy, i.e., administered to a patient who is in remission.

In certain embodiments, the methods include treating one or more autoimmune disease. In one embodiment, the autoimmune disorder is inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia.

In other embodiment, the methods include treating one or more heteroimmune disorder. In one embodiment, the heteroimmune disorder is graft versus host disease, transplantation, transfusion, anaphylaxis, allergy, type I hypersensitivity, allergic conjunctivitis, allergic rhinitis, or atopic dermatitis.

In certain embodiments, the methods include treating one or more inflammatory disease. In one embodiment, the inflammatory disease is arthritis, asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In still other embodiments, the methods include treating one or more cancer. In one embodiment, the cancer is a B-cell proliferative disorder. In still another embodiment, the cancer is a hematological malignancy. In a further embodiment, the cancer is B-cell prolymphocytic leukemia, leukemia, lymphoma, lymphoproliferative disorder, lymphoplasmacytic lymphoma, Waldenstrom macroglobulinemia, myeloid disorder, plasma cell myeloma, plasmacytoma, mediastinal large B cell lymphoma, intravascular large B cell lymphoma, primary effusion lymphoma, lymphomatoid granulomatosis, non-Hodgkin's CLL, SLL, high risk CLL, non-CLL/SLL lymphoma, follicular lymphoma, diffuse large B-cell lymphoma, mantle cell lymphoma, multiple myeloma, marginal zone lymphoma, non-Burkitt high grade B cell lymphoma, extranodal marginal zone B cell lymphoma, acute or chronic myelogenous leukemia, myelodysplastic syndrome, lymphoblastic leukemia, relapsed or refractory diffuse large B-cell lymphoma, relapsed or refractory mantle cell lymphoma, relapsed or refractory follicular lymphoma, relapsed or refractory CLL, relapsed or refractory SLL, relapsed or refractory multiple myeloma, Burkitt's lymphoma, cutaneous B-cell lymphoma, cutaneous marginal zone lymphoma, diffuse mixed small and large cell lymphoma, diffuse small cleaved cell, extranodal follicular small cleaved cell, follicular mixed small cleaved and large cell, follicular large cell, intravascular lymphomatosis, large cell immunoblastic lymphoma, large cell lymphoma, mucosa associated lymphoid tissue Lymphoma, immunoblastic large cell lymphoma, precursor B-lymphoblastic lymphoma, chronic lymphocytic leukemia/small lymphocytic lymphoma, nodal marginal zone B-cell lymphoma, splenic marginal zone B-cell lymphoma, primary mediastinal B-cell lymphoma, hairy cell leukemia, and primary central nervous system lymphoma. In another embodiment, the B-cell proliferative disorder is non-Hodgkin lymphoma, Waldenstrom macroglobulinemia, plasma cell myeloma, or chronic lymphocytic leukemia. In a further embodiment, the B-cell proliferative disorder is diffuse large B cell lymphoma, follicular lymphoma, mantle cell lymphoma and Burkitt lymphoma. In still another embodiment, the cancer is leukemia. In yet another embodiment, the cancer is a lymphoma.

In yet other embodiments, the methods include treating a thromboembolic disorder. In one embodiment, the thromboembolic disorder is myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

The dosage requirements of Ibrutinib may vary based on the severity of the symptoms presented and the particular subject being treated. Treatment may be initiated with small dosages less than the optimum dose of Ibrutinib. Thereafter the dosage may be increased until the optimum effect under the circumstances is reached. Precise dosages will be determined by the administering physician based on experience with the individual subject treated. In one embodiment, the composition is administered at a concentration that will afford effective results without causing any unacceptable harmful or deleterious side effects.

The term "effective amount," as used herein, refers to a sufficient amount of an agent or a compound being administered which will relieve one or more symptom of a B-cell proliferative disorder. The result may be reduction and/or alleviation of the signs, symptoms, or causes of the disorder. In certain embodiments, the effective amount achieves the desired pharmacologic effect or therapeutic improvement without undue adverse side effects.

An effective amount of Ibrutinib can vary depending on the components of the composition, mode of delivery, severity of the condition being treated, the patient's age and weight, and any other active ingredients used in the composition. The dosing regimen can also be adjusted to provide the optimal therapeutic response. Several divided doses may be delivered daily, e.g., in divided doses 2 to 4 times a day, or a single dose can be delivered. The dose can however be proportionally reduced or increased as indicated by the exigencies of the therapeutic situation. In one embodiment, the delivery is on a daily, weekly, or monthly basis. In another embodiment, the delivery is on a daily delivery. The composition may be administered daily. In some embodiments, the composition may be administered every other day. In some embodiments, the composition may be administered once or more times per day. In some embodiments, the composition may be administered two or more times per day. In some embodiments, the composition may be administered three or more times per day.

The dosages may also be lowered or raised based on the periodic delivery. The attending physician also has the flexibility to continue the same administration for a period of time or may decide to alter the administration schedule. This may be as a result of improved conditions, adverse, but not fatal, reactions to the composition, or the like. If administration is halted, re-administration may be continued if the patient stabilizes or improvement of the condition has materialized. Accordingly, the dosage, frequency of administration, or combination thereof may be reduced or increased as needed.

The amount of Ibrutinib administered may vary depending upon severity of the disease, weight of the subject, age of the subject, among others. In one embodiment, an effective amount is about 0.1 to about 5000 mg/day. In one embodiment, an effective amount of Ibrutinib is about 1 to about 1500 mg/day. In another embodiment, the effective amount of Ibrutinib is about 20 to about 450 mg/day. In a further embodiment, the effective amount of Ibrutinib is about 20 to about 420 mg/day. In yet another embodiment, the effective amount of Ibrutinib is about 30 to about 300 mg/day. In still a further embodiment, the effective amount of Ibrutinib is about 50 to about 200 mg/day. In another embodiment, the effective amount of Ibrutinib is about 70 to about 140 mg/day.

The desired dose may conveniently be presented in a single dose or as divided doses administered simultaneously (or over a short period of time) or at appropriate intervals, for example as two, three, four or more sub-doses per day.

The compositions may be delivered to the subject by any suitable route as directed by the attending physician. In one embodiment, the compositions are delivered orally.

The compositions may be co-administered with one or more of a second agent. The second agent may be administered prior to, concurrently with, or subsequent to the compositions discussed herein. In some embodiments, the second agent comprises a chemotherapeutic agent, steroid, immunotherapeutic agent, among others. In another embodiment, the second agent is one or more of actinomycines, alkylating agents, alitretinoin, altretamine, amzacrine, anagrelide, angiogenesis inhibitors, antibody, anti-androgens, anti-estrogens, antimetabolites, anthracyclines, arsenic trioxide, asparaginase, B cell receptor pathway inhibitor (CD79A inhibitor, CD79B inhibitor, CD 19 inhibitor, Lyn inhibitor, Syk inhibitor, PI3K inhibitor, Blnk inhibitor, PLCγ inhibitor, PKCβ inhibitor), basiliximab, bexarotene, bortezomib, calcineurin inhibitors, canakinumab, celecoxib, ceradenovec, colchicine derivatives, cytotoxic antibiotics, daclizumab, denileukin diftitox, DNA damaging agent, epoxides, estramustine, estrogens, ethylene imines, folic acid analogues, gonadotropin releasing interferons, growth factors, HDAC inhibitor, hedgehog inhibitor, Hsp90 inhibitor, histone deacetylase inhibitor, hormones, hormone analogs, hormone antagonists, hydroxycarbamide, IAP inhibitor, ibritumomab immunostimulants, immunosuppressants, interleukin inhibitors, interleukins, irinotecan, Jak1/2 inhibitor, lonidamine, masoprocol, mepolizumab, miltefosein, mitoguazone, mitotane, monoclonal antibodies, mTOR inhibitor, methylhydrazines, nitrogen mustards, nitrosoureas, PI3K inhibitor, oblimersen, PARP inhibitor, pegaspargase, pentostatin, PKC inhibitor, plant alkaloids, platinum compounds (carboplatin, cisplatin, oxaliplatin, or satraplatin), podophyllotoxin derivatives, progestogens, proteasome inhibitor, protein kinase inhibitor, protease inhibitor, purine analogs, pyrimidine analogs, radioimmunotherapeutic, sensitizers, romidepsin, sitimagene tiazofurine, topotecan, tretinoin, tumor necrosis factors, TNF-α Inhibitors, tocilizumab, telomerase inhibitor, tiuxetan, tositumomabtriazenes, ustekinumab, vinca alkaloids, or vorinostat. In a further embodiment, the second agent includes, Adriamycin, dactinomycin, bleomycin, Vinblastine, Cisplatin, acivicin; aclarubicin; acodazole hydrochloride; acronine; adozelesin; aldesleukin; alemtuzumab; altretamine; ambomycin; ametantrone acetate; aminoglutethimide; amsacrine; anastrozole; anthramycin; asparaginase; asperlin; azacitidine; azetepa; azotomycin; batimastat; bendamustine, bevacizumab; benzodepa; bicalutamide; bisantrene hydrochloride; bisnafide dimesylate; bizelesin; bleomycin sulfate: brequinar sodium; bropirimine; busulfan; cactinomycin; calusterone; caracemide; carbetimer; carboplatin; carmustine; carubicin hydrochloride; carzelesin; cedefingol; cetuximab; chlorambucil; cirolemycin; cladribine; crisnatol mesylate; Crizotinib; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride: elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; 5-fluorouracil; fosquidone; fostriecin sodium; gemcitabine; gemcitabine hydrochloride; gemtuzamab; hydroxyurea; idarubicin hydrochloride; ifosfamide; ilmofosine; interleukin II, interferon α-2a; interferon α-2b; interferon α-n1; interferon α-n3; interferon β-1 a; interferon γ-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; Nexavar®; nocodazoie; nogalamycin; ofatumumab; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rituaximab; rogletimide; safingol; safingol hydrochloride; semustine; simtrazene; sparfosate sodium; sparsomycin; spirogermanium hydrochloride; spiromustine; spiroplatin; Sprycel®; streptonigrin; streptozocin; sulofenur; Sutent®; talisomycin; Tarceva®; tecogalan sodium; tegafur; teloxantrone hydrochloride; temoporfin; temozolomide; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; Tykerb®; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; wortmannin; zeniplatin; zinostatin; zorubicin hydrochloride.

G. Kits Containing the Compositions

Also provided are kits or packages containing Ibrutinib and an optional carrier suitable for administration to a mammalian subject as discussed above. In one embodiment, the capsules may be packaged in bottles, blister packs, pill boxes, or the like. In another embodiment, the liquid formulation may be packaged in a bottle optionally coated with a piercable cap, ampule, drop counter, or in a saline bag.

The kits or packages containing the compositions described herein are designed for use in the methods described herein. The kit can optionally further contain instructions for administering composition, a carrier suitable for administration of the composition, one or more instruments including, without limitation, syringe, pipette, forceps, measuring spoon, or the like. Other components for inclusion in the kits would be clear to those skilled in the art, taking into consideration the desired indication and mode of delivery.

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

EXAMPLES

Example 1: Solid Compositions Containing Ibrutinib

Solid compositions containing Ibrutinib were prepared for inclusion in a capsule as described in the following.

A. 140 mg Capsule

In this process, an intragranular blend was prepared by mixing MCC (151.49 mg; Avicel PH 101), SLS (9.40 mg; Kolliphor; fine), and CCS (13.10 mg; Ac-di-sol) in a vessel. This was then mixed with Ibrutinib (70 mg; micronized, Lonza, Nansha). The remaining Ibrutinib (70 mg) was then added and the composition mixed. Magnesium stearate (0.8 mg; Non-Bovine #5712) was then added to this mixture and the same blended to provide a pre-roller compaction blend. The pre-roller compaction blend was then roller compacted to form ribbons. The ribbons were then milled to provide a composition containing granules.

The granules were then blended with a second portion of SLS (4.6 mg; Kolliphor; fine) and CCS (9.9 mg; Ac-di-sol). To this blend was then added a second portion of magnesium stearate (0.8 mg; Non-Bovine #5712) to provide a lubricated blend. This lubricated blend was then added to a size 0 Swedish orange hard gelatin capsule.

B. 50 mg Ibrutinib Capsule

In this process, an intragranular blend was prepared by mixing MCC (54.07 mg; Avicel PH 101), SLS (3.36 mg; Kolliphor; fine), and CCS (4.68 mg; Ac-di-sol). This was then mixed with Ibrutinib (25 mg; micronized, Lonza, Nansha). The remaining Ibrutinib (25 mg) was then added and the composition mixed. Magnesium stearate (0.29 mg; Non-Bovine #5712) was then added to this mixture and the same blended to provide a pre-roller compaction blend. The pre-roller compaction blend was then roller compacted to form ribbons. The ribbons were then milled to provide a composition containing granules.

The granules were then blended with a second portion of SLS (1.64 mg; Kolliphor; fine) and CCS (3.54 mg; Ac-di-sol). To this blend was then added magnesium stearate (0.29 mg; Non-Bovine #5712) to provide a lubricated blend. This lubricated blend (117.87 mg) was then added, independently, to a size 0 Swedish orange hard gelatin capsule and a Swedish orange sprinkle capsule.

Example 2: Liquid Suspension Composition Containing Ibrutinib (i) 70 mg/mL Ibrutinib Liquid Suspension A liquid composition containing 70 mg/mL of Ibrutinib was prepared. Specifically, water (300 mL) was mixed with a composition MCC of CCS (Avicel RC591; 6.5 g) for 30 minutes. This dispersion was then homogenized for 30 seconds using a SILVERSON® homogenizer L2R at the maximal speed (7500 rpm). HPMC (2910 5 mPas; 1.25 g) was mixed with water (120 mL) until homogeneous using a magnetic stirrer. Micronized Ibrutinib (35 g, Lonza Clinical) was then added to the HPMC solution and mixed for 120 minutes. The MCC/CCS dispersion was then mixed with the Ibrutinib mixture. Sucralose (0.5 g), sodium methyl parahydroxybenzoate (0.5725 g), and sodium ethyl parahydroxybenzoate (0.2875 g) were added to the mixture. After about 10 minutes stirring, citric acid monohydrate (0.7565 g), and disodium hydrogen phosphate anhydrous parenteral (0.69 g) were then added to this mixture. The mixture was stirred for about 10 minutes until the content solubilized. The pH of the mixture was measured and found to be 5.99, thereby eliminating the need to adjust the pH. The mixture was then diluted with purified water until a final weight of 510.5 g. The mixture was again measured and found to be about 6.

The concentration for each component in the final liquid composition is provided in Table 2.

(ii) 40 mg/mL Ibrutinib Liquid Suspension

A liquid composition containing 40 mg/mL of Ibrutinib was prepared. Specifically, water (300 mL) was mixed with a composition MCC of CCS (Avicel RC591; 7 g) for 30 minutes. This dispersion was then homogenized for 30 seconds using a SILVERSON® homogenizer L2R at the maximal speed (7500 rpm). HPMC (2910 5 mPas; 0.5 g) was mixed with water (120 mL) until homogeneous using a magnetic stirrer. Micronized Ibrutinib (20 g, Lonza Clinical) was then added to the HPMC solution and mixed for 120 minutes. The MCC/CCS dispersion was then mixed with the Ibrutinib mixture. Sucralose (0.25 g), sodium methyl parahydroxybenzoate (0.6791 g) and sodium ethyl parahydroxybenzoate (0.3387 g) were added to the mixture. After about 10 minutes stirring, citric acid monohydrate (0.801 g), and disodium hydrogen phosphate anhydrous parenteral (0.69 g) were then added to this mixture. The mixture was stirred for about 10 minutes until the contents solubilized. The pH of the mixture was measured and found to be about 5.99, thereby eliminating the need to adjust the pH. The mixture was then diluted with purified water until final weight of 507 g. This mixture was then homogenized. The pH was again measured and found to be about 6.

The concentration for each component in the final liquid composition is provided in Table 3.

Example 3: Large Scale Preparation of a Suspension Containing Ibrutinib Preparation of 4 L Batch Purified water (480 g) was added to a vessel and warmed to about 83° C. at a stirring rate of about 400 rpm for about 60 minutes. HPMC (10.002 g) was slowly added to the vessel and the mixture stirred at a rate of about 7600 rpm for about 4 minutes until the mixture was homogenized. To this vessel was added purified water (480 g) and then mixture was stirred for about 5 minutes at a rate of about 500 rpm at room temperature until the mixture was solubilized. Ibrutinib (278.6 g) was added to the mixture and it was stirred at 600 rpm for about 2 h until it was homogenous. The mixture was monitored using a microscope for agglomerates.

Purified water (2400 g) was then added to a second vessel. At a rate of about 500 rpm, MCC (51.74 g; Avicel) was added to the second vessel over a period of 3 minutes, followed by stirring at a rate of about 400 rpm for about 60 minutes. This mixture was then homogenized using a stirring speed of about 7600 tr/min over a period of about 4 minutes. The mixture was monitored using a microscope for agglomerates.

The mixture in the first vessel was then added to the mixture in the second vessel and the combined contents stirred for about 5 minutes at a speed of about 500 rpm. The first vessel was then rinsed using purified water (200 ml) and the same added to the second vessel. Under moderate stirring conditions, sucralose (4.0038 g), sodium methyl parahydroxybenzoate (4.5838 g), and sodium ethyl parahydroxybenzoate (2.300 g) were sequentially added to the second vessel and the mixture stirred for about 11 minutes until the solids solubilized. Citric acid monohydrate (6.052 g) was then added to the second vessel and the mixture stirred for about 10 minutes. Anhydrous disodium hydrogen phosphate (5.521 g) was then added and the mixture was stirred for about 10 minutes until the contents solubilized. The pH of the solution was measured and found to be about 5.94, thereby eliminating the need to adjust the pH.

Figure 3:
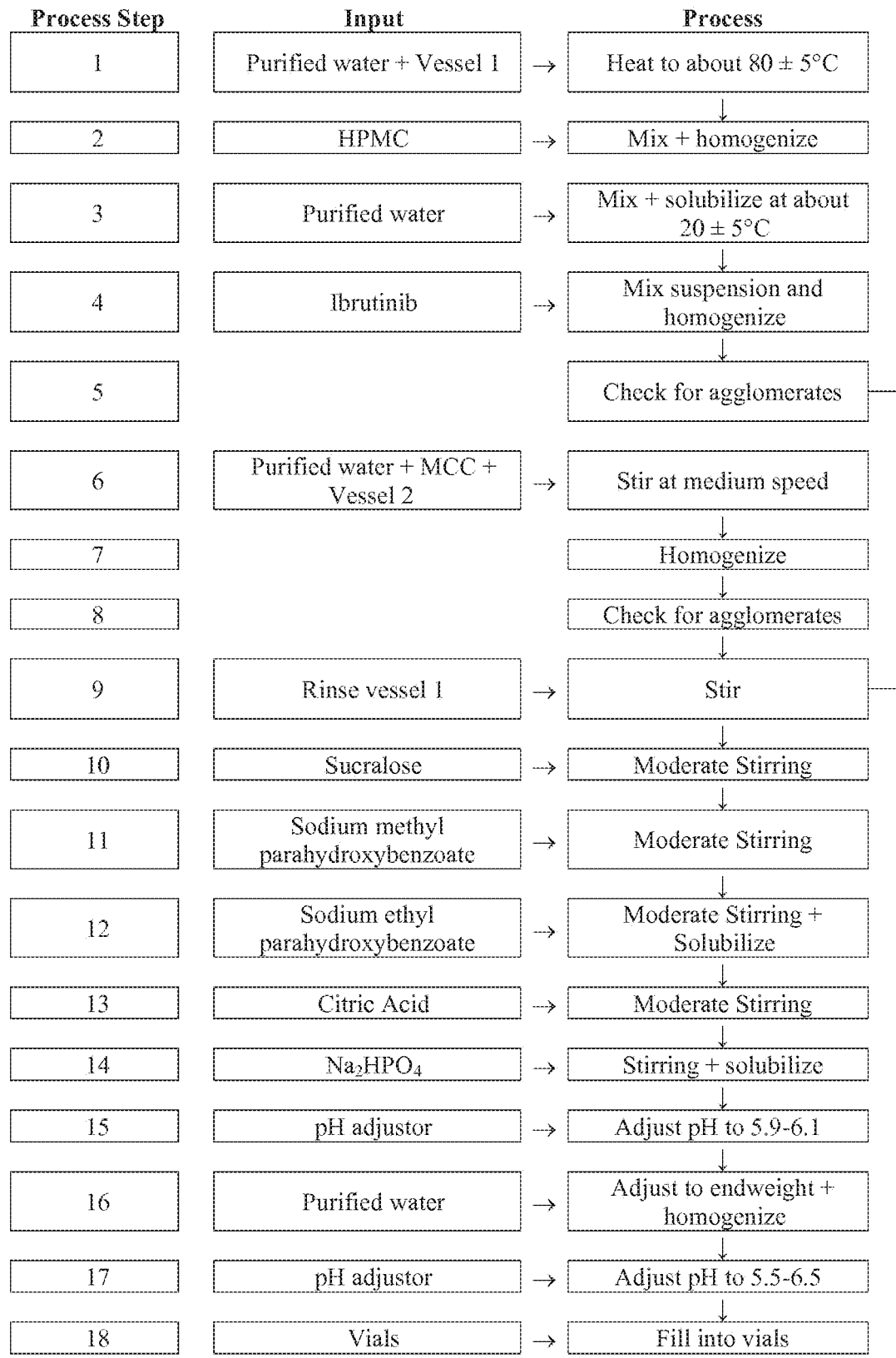
FIG. 3 provides a process flow diagram for a large scale preparation of a liquid formulation containing Ibrutinib.

The mixture was then diluted using purified water (4064 g) until a final weight of 4084 g. This mixture was then homogenized. The pH was again measured and found to be about 5.98. Aliquots (8 ml) of the mixture were then removed under constant stirring at a speed of about 500 to about 1300 rpm over a period of about 75 minutes. Each aliquot was added to a an amber, glass vial (10 ml), a Flurotec coated rubber injection stopper (20 mm) then inserted into the vial, and the stopper affixed with an aluminum tear-off cap (20 mm). See, FIG. 3.

Example 4: Stability Studies of Ibrutinib Formulations

The stability of the solid composition described herein was evaluated in 3 liquids. Specifically, the contents of 4 sprinkle capsules described herein (each containing 140 mg of solid composition) were dissolved in water (100 mL), milk (100 mL), and orange juice (100 mL) at room temperature. After about 6 hours, the colors of the milk and orange juice solutions remained unchanged, while the water solution turned milky white.

It was found using liquid chromatography that the three Ibrutinib formulations were stable. Specifically, most of the Ibrutinib active agent with minor amounts of impurities was recovered from these formulations after sitting for 6 hours.

Example 5: Feeding Tube Studies Using Ibrutinib Formulations

Feasibility studies were conducted on feeding tubes using a composition described herein. Specifically, two formulations were prepared, each formulation containing water (20 mL) and the contents of 4 sprinkle capsules described herein (total of 560 mg of active equivalent granules). Upon passing the formulations through size 2.2 mm and 2.7 mm ID feeding tubes, it was observed that the formulations (containing the water and composition) passed through the tubes by gravity force and without clogging.

It was also found that the tubes could be re-used before the introduction of another formulation. Specifically, air was blown through the tubes by applying a small amount of pressure using a syringe. Additional formulations could then be passed through the tubes without any interruption. It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed is:

1. A stable pharmaceutical composition in the form of a suspension, comprising:
   about 30 to about 80 mg/mL of ibrutinib suspended in one or more suspending agents;
   one or more wetting agents;
   one or more buffering agents; and
   one or more preservatives.

2. The stable pharmaceutical composition of claim 1, comprising about 70 mg/mL of the ibrutinib.

3. The stable pharmaceutical composition of claim 1, comprising at least two suspending agents.

4. The stable pharmaceutical composition of claim 1, comprising about 12 to about 15 mg/mL of the one or more suspending agents.

5. The stable pharmaceutical composition of claim 4, comprising about 12 mg/mL of the one or more suspending agents.

6. The stable pharmaceutical composition of claim 1, comprising about 0.5 to about 3 mg/mL of the one or more wetting agents.

7. The stable pharmaceutical composition of claim 6, comprising about 0.5 to about 2.5 mg/mL of the one or more wetting agents.

8. The stable pharmaceutical composition of claim 7, comprising about 2.5 mg/mL of the one or more wetting agents.

9. The stable pharmaceutical composition of claim 1, comprising at least two buffering agents.

10. The stable pharmaceutical composition of claim 1, further comprising one or more sweeteners.

11. The stable pharmaceutical composition of claim 10, comprising about 0.1 to about 1.5 mg/mL of the one or more sweeteners.

12. The stable pharmaceutical composition of claim 11, comprising about 0.5 to about 1.5 mg/mL of the one or more sweeteners.

13. The stable pharmaceutical composition of claim 12, comprising about 1 mg/mL of the one or more sweeteners.

14. The stable pharmaceutical composition of claim 1, further comprising one or more diluents.

15. The stable pharmaceutical composition of claim 1, wherein the diluent is water.

16. The stable pharmaceutical composition of claim 1, wherein the pH is about 5.5 to about 6.5.

17. The stable pharmaceutical composition of claim 16, wherein the pH is about 6.

18. The stable pharmaceutical composition of claim 17, wherein the pH is about 6 and does not comprise a pH adjustor.

19. The stable pharmaceutical composition of claim 16, that degrades less than about 3% under light irradiation.

20. The stable pharmaceutical composition of claim 16, that is stable at about 20° C./50% relative humidity to about 45° C./75% relative humidity.

21. The stable pharmaceutical composition of claim 16, that is stable over a period of greater than 1 month at temperatures at or greater than about 25° C. and a relative humidity at or greater than about 60%.

22. A stable pharmaceutical composition in the form of a suspension, the composition comprising: about 70 mg/mL of the ibrutinib suspended in about 12 to about 15 mg/mL of the one or more suspending agents; and
    one or more wetting agents;
    one or more buffering agents; and
    one or more preservatives.

23. The stable pharmaceutical composition of claim 22, further comprising about 0.5 to about 3 mg/mL of the one or more wetting agents.

24. The stable pharmaceutical composition of claim 23, further comprising water.

25. The stable pharmaceutical composition of claim 22, wherein the pH is about 5.5 to about 6.5.

26. The stable pharmaceutical composition of claim 25, wherein the pH is about 6.

27. The stable pharmaceutical composition of claim 26, wherein the pH is about 6 and does not comprise a pH adjustor.

* * * * *